US009670251B2

(12) United States Patent
Hay et al.

(10) Patent No.: US 9,670,251 B2
(45) Date of Patent: *Jun. 6, 2017

(54) ANG-(1-7) DERIVATIVE OLIGOPEPTIDES AND METHODS FOR USING AND PRODUCING THE SAME

(71) Applicant: The Arizona Board of Regents on Behalf of the University of Arizona, Tucson, AZ (US)

(72) Inventors: Meredith Hay, Tucson, AZ (US); John Konhilas, Tucson, AZ (US); Robin L. Polt, Tucson, AZ (US); Evan Jones, Tucson, AZ (US)

(73) Assignee: The Arizona Board of Regents on behalf of the University of Arizona, Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/134,073

(22) Filed: Apr. 20, 2016

(65) Prior Publication Data

US 2016/0347794 A1    Dec. 1, 2016

Related U.S. Application Data

(63) Continuation of application No. 14/801,557, filed on Jul. 16, 2015.

(60) Provisional application No. 62/027,219, filed on Jul. 21, 2014.

(51) Int. Cl.
| | |
|---|---|
| *C07K 7/14* | (2006.01) |
| *C07K 7/06* | (2006.01) |
| *C07K 7/00* | (2006.01) |
| *A61K 38/00* | (2006.01) |
| *C07K 9/00* | (2006.01) |

(52) U.S. Cl.
CPC ............... *C07K 7/14* (2013.01); *C07K 7/06* (2013.01); *C07K 9/001* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,629,292 A | 5/1997 | Rodgers et al. | |
| 5,716,935 A | 2/1998 | Rodgers et al. | |
| 5,834,432 A | 11/1998 | Rodgers et al. | |
| 5,955,430 A | 9/1999 | Rodgers et al. | |
| 6,096,709 A | 8/2000 | Rodgers et al. | |
| 6,110,895 A | 8/2000 | Rodgers et al. | |
| 6,165,978 A | 12/2000 | Rodgers et al. | |
| 6,177,407 B1 | 1/2001 | Rodgers et al. | |
| 6,239,109 B1 | 5/2001 | Rodgers et al. | |
| 6,248,587 B1 | 6/2001 | Rodgers et al. | |
| 6,258,778 B1 | 7/2001 | Rodgers et al. | |
| 6,335,195 B1 | 1/2002 | Rodgers et al. | |
| 6,444,646 B1 | 9/2002 | Rodgers et al. | |
| 6,455,500 B1 | 9/2002 | Rodgers et al. | |
| 6,455,501 B1 | 9/2002 | Rodgers et al. | |
| 6,475,988 B1 | 11/2002 | Rodgers et al. | |
| 6,482,800 B1 | 11/2002 | Rodgers et al. | |
| 6,498,138 B1 | 12/2002 | Rodgers et al. | |
| 6,566,335 B1 | 5/2003 | Rodgers et al. | |
| 6,730,775 B1 | 5/2004 | Rodgers et al. | |
| 6,747,008 B1 | 6/2004 | Rodgers et al. | |
| 6,762,167 B1 | 7/2004 | Rodgers et al. | |
| 6,821,953 B1 | 11/2004 | Rodgers et al. | |
| 6,916,783 B2 | 7/2005 | Rodgers et al. | |
| 7,022,675 B2 | 4/2006 | Rodgers et al. | |
| 7,118,748 B1 | 10/2006 | Rodgers et al. | |
| 7,122,523 B2 | 10/2006 | Rodgers et al. | |
| 7,173,011 B2 | 2/2007 | Rodgers et al. | |
| 7,176,183 B2 | 2/2007 | Rodgers et al. | |
| 7,288,522 B1 | 10/2007 | Rodgers et al. | |
| 7,338,938 B2 | 3/2008 | Rodgers et al. | |
| 7,744,927 B2 | 6/2010 | Rodgers et al. | |
| 8,633,158 B1 | 1/2014 | Franklin | |
| 2004/0214272 A1* | 10/2004 | La Rosa | C07H 21/04 435/69.1 |
| 2005/0153890 A1 | 7/2005 | Pan et al. | |
| 2008/0312129 A1 | 12/2008 | Souza Dos Santos et al. | |
| 2010/0055146 A1* | 3/2010 | Haas | A61L 31/16 424/423 |

(Continued)

FOREIGN PATENT DOCUMENTS

| | | |
|---|---|---|
| JP | 2011-500677 A | 1/2011 |
| JP | 2013-047249 A | 3/2013 |

(Continued)

OTHER PUBLICATIONS

Sola 2009 "effects of glycocylation on the stability of protein pharmaceuticals" j pharm sci 98(4):1223-1245.*
Japanese Office Action, Application No. 2016-524300, Nov. 1, 2016.
Extended European Search Report, Application No. 14820282.3, Dec. 12, 2016.
Albrecht, "Angiotensin-(1-7)-induced plasticity changes in the lateral amygdala are mediated by COX-2 and NO", Learning and Memory, vol. 14, No. 3, (Mar. 2007) pp. 177-184.
Bodiga, et al., "Renin Angiotensin System in Cognitive Function and Dementia," Asian J. of Neurosci., vol. 19, No. 10 (2013) pp. 3952-3962.
Ciobica, et al., "Brain renin-angiotensin system in cognitive function: pre-ciinical findings and implications for prevention and treatment of dementia", ACTA Neurol. Belg., vol. 109 (Jan. 2009) pp. 171-180.

(Continued)

*Primary Examiner* — Adam M Weidner
(74) *Attorney, Agent, or Firm* — Orrick, Herrington & Sutcliffe LLP

(57) ABSTRACT

The present invention provides oligopeptides, in particular, Ang-(1-7) derivatives, and methods for using and producing the same. In one particular embodiment, oligopeptides of the invention have higher blood-brain barrier penetration and/or in vivo half-life compared to the native Ang-(1-7), thereby allowing oligopeptides of the invention to be used in a wide variety of clinical applications including in treatment of cognitive dysfunction and/of impairment.

21 Claims, 4 Drawing Sheets

(56) References Cited

U.S. PATENT DOCUMENTS

| | | | |
|---|---|---|---|
| 2011/0281805 A1* | 11/2011 | Walther | A61K 31/4178 514/21.7 |
| 2012/0129776 A1 | 5/2012 | Cohen et al. | |
| 2013/0137637 A1* | 5/2013 | Cho | C07K 7/06 514/13.3 |
| 2013/0183683 A1* | 7/2013 | Pemberton | C07K 14/58 435/7.4 |
| 2013/0184208 A1* | 7/2013 | Alaoui-Ismaili | C07K 14/51 514/8.8 |
| 2013/0184212 A1* | 7/2013 | Camphausen | C07K 14/78 514/9.3 |

FOREIGN PATENT DOCUMENTS

| | | |
|---|---|---|
| WO | WO 02/06308 A2 | 1/2002 |
| WO | WO 2009/114461 A2 | 9/2009 |
| WO | WO 2012/021578 A1 | 2/2012 |
| WO | WO 2012/070936 A | 5/2012 |
| WO | WO 2013/090833 A | 6/2013 |
| WO | WO 2013/119870 A1 | 8/2013 |
| WO | WO 2013/172956 A1 | 11/2013 |
| WO | WO 2014/021942 A1 | 2/2014 |
| WO | WO 2014021942 * | 2/2014 |
| WO | WO 2014/055591 A1 | 4/2014 |
| WO | WO 2014/115587 A1 | 9/2014 |
| WO | WO 2014/151338 A1 | 9/2014 |
| WO | WO 2014/179440 | 11/2014 |
| WO | WO 2016/112247 A1 | 7/2016 |

OTHER PUBLICATIONS

Ciobica, et al., "The Effects of Angiotensin II and Angiotensin 1-7 in Cognitive Processes and Oxidative Stress in Rates, Relevance for Alzheimer's Disease", Alzheimer's & Dementia: The Journal of the Aizheimer's Association, vol. 7, No. 4 (Jul. 2011) pp. S112-S113.

Fontes, et al., "Evidence that angiotensin-(1-7) plays a role in central control of blood pressure at the ventro-lateral medulla acting through specific receptors," Brain Research. vol. 665 (Nov. 1994) pp. 175-180.

Hellner, et al., "Angiotensin-(1-7) enhances LTP in the hippocampus through the G-protein-coupled receptor Mas", Mol. Cell. Neurosci, vol. 29, No. 3 (Jul. 2005) pp. 427-435.

Jiang, et al., "ACE2-Ang-(1-7)-Mas Axis in Brain: A Potential Target for Prevention and Treatment of ischemic Stroke," Current Neuropharmacology, (Jan. 2013) pp. 209-217.

Lazaroni, et al., "Angiotensin-(1-7)/Mas axis integrity is required for the expression of object recognition memory," Neurobiology of Learning & Memory, vol. 97, No. 1 (Oct. 2011) pp. 113-123, San Diego, CA, US.

Passos-Silva, et al., "Angiotensin-(1-7): beyond the cardio-renal actions," Clin. Sci., vol. 124, (2013) pp. 443-456, Great Britain.

Silva, et al., "Promising Neuroprotective Effects of the Angiotensin 1-7/ACE2/Mas axis in Stroke", Exp. Physiol. vol. 99, No. 2 (Feb. 2014) pp. 342-343.

Xie, et al., "Angiotensin-(1-7) improves cognitive function in rats with chronic cerebral hypoperfusion," Brain Research, vol. 1573 (May 2014) pp. 44-53.

Xu, et al., "ACE2/ANG-(1-7)/Mas pathway in the brain: the axis of good," Am. J. Physiol. Regul. Integr. Comp. Physiol., vol. 300 (Dec. 2010) pp. R804-R817.

* cited by examiner

ANG-(1-7) DERIVATIVE OLIGOPEPTIDES AND METHODS FOR USING AND PRODUCING THE SAME

CROSS-REFERENCE TO RELATED APPLICATIONS

This application is a continuation of U.S. application Ser. No. 14/801,557, filed Jul. 16, 2015, which claims the priority benefit of U.S. Provisional Application No. 62/027,219, filed Jul. 21, 2014, all of which are incorporated herein by reference in their entirety.

FIELD OF THE INVENTION

The present invention relates to oligopeptides, such as Ang-(1-7) derivatives, and methods for using and producing the same. In one particular embodiment, oligopeptides of the invention have higher blood-brain barrier penetration and/or longer in vivo half-life compared to the native Ang-(1-7), thereby allowing compounds of the invention to be used in a wide variety of clinical applications to treat cognitive dysfunction and/or impairment.

BACKGROUND OF THE INVENTION

Cognitive dysfunction or impairment is a common neurological complication of congestive heart failure ("CHF") and post cardiac surgery affecting approximately 50-70% of patients at hospital discharge and 20-40% of patients six months after surgery. The occurrence of CHF and postoperative cognitive dysfunction is associated with increased duration of hospitalization and impaired long-term quality of life. Without being bound by any theory, it is believed that in general any clinical condition associated with an increase in inflammatory cytokines and/or increase in reactive oxygen species in central nervous system, in particular in the brain, can lead to cognitive dysfunction.

Unfortunately, currently there is no effective pharmacological treatment for cognitive impairment or dysfunction for CHF and postoperative patients or for any other clinical condition associated with an increase in inflammation cytokines and/or increase in reactive oxygen species in the brain.

The present inventors have shown that CHF results in a significant impairment of both spatial memory and object recognition ability. The present inventors have also discovered that systemic administration of native Ang-(1-7) attenuates CHF-induced spatial memory and object recognition impairment. In addition, Mas, the receptor for Ang-(1-7), is known to be expressed in the hippocampus. In addition, other researchers using two different rat models have shown that Ang-(1-7) protects the cortex against reactive oxygen species ("ROS")-mediated damage from cerebral ischemia. This strongly implicates that the neuroprotective ability of Ang-(1-7) against CHF-induced cognitive impairment is mediated by central activation of the Ang-(1-7)/Mas signaling axis at both the vascular endothelial and neuronal levels.

Unfortunately, it is generally well known that oligopeptides, such as Ang-(1-7) are relatively easily degraded in vivo and/or are not suitable for conventional administration as Ang-(1-7) cannot readily cross the blood-brain barrier.

Accordingly, there is a need for Ang-(1-7) derivatives that can relatively readily cross the blood-brain barrier and/or have a substantially longer in vivo half-life compared to the native Ang-(1-7).

SUMMARY OF THE INVENTION

Some aspects of the invention provide an oligopeptide that is angiotensin-(1-7), i.e., "Ang-(1-7)", derivative. Oligopeptides of the invention have a longer in vivo half-life and/or increased blood-brain barrier penetration than Ang-(1-7). In some embodiments, the oligopeptides of the invention have seven or eight amino acids.

One particular aspect of the invention provides an oligopeptide derivative of the formula: $A^1$-$A^2$-$A^3$-$A^4$-$A^5$-$A^6$-$A^7$-$A^8$ (SEQ ID NO:1), where $A^1$ is selected from the group consisting of aspartic acid, glutamic acid, alanine, and a derivative thereof; $A^2$ is selected from the group consisting of arginine, histidine, lysine, and a derivative thereof; $A^3$ is selected from the group consisting of valine, alanine, isoleucine, leucine, and a derivative thereof; $A^4$ is selected from the group consisting of tyrosine, phenylalanine, tryptophan, and a derivative thereof; $A^5$ is selected from the group consisting of isoleucine, valine, alanine, leucine, and a derivative thereof; $A^6$ is selected from the group consisting of histidine, arginine, lysine, and a derivative thereof; $A^7$ is selected from the group consisting of proline, glycine, serine, and a derivative thereof; and $A^8$ can be present or absent, wherein when $A^8$ is present, $A^8$ is selected from the group consisting of serine, threonine, hydroxyproline, and a derivative thereof, provided (i) at least one of $A^1$-$A^8$ is optionally substituted with a mono- or di-carbohydrate; or (ii) when $A^8$ is absent: (a) at least one of $A^1$-$A^7$ is substituted with a mono- or di-carbohydrate, (b) $A^7$ is terminated with an amino group, or (c) a combination thereof.

In some embodiments, carbohydrate comprises glucose, galactose, xylose, fucose, rhamnose, lactose, cellobiose, melibiose, or a combination thereof. In another embodiment, $A^8$ is serine or a derivative thereof.

Still in other embodiments, (i) $A^8$ is terminated with an amino group; or (ii) when $A^8$ is absent, $A^7$ is terminated with an amino group. Within these embodiments, in some instances (i) $A^8$ is serine that is glycosylated with glucose or lactose; or (ii) when $A^8$ is absent, $A^7$ is serine that is glycosylated with glucose or lactose. Still in other instances, when $A^8$ is absent and $A^7$ serine that is glycosylated with glucose. Within the latter instances, in some cases $A^7$ is terminated with an amino group.

Yet in other embodiments, $A^1$ is aspartic acid; $A^2$ is arginine; $A^3$ is valine; $A^4$ is tyrosine; $A^5$ is isoleucine; $A^6$ is histidine; and (i) $A^8$ is absent and $A^7$ is terminated with an amino group or $A^7$ is a glycosylated serine, or (ii) $A^8$ is serine terminated with an amino group. Within these embodiments, in some cases $A^8$ is a glycosylated serine. Still in other cases, $A^8$ is absent and $A^7$ is a glycosylated serine that is terminated with an amino group.

Another aspect of the invention provides a glycosylated Ang-(1-7) derivative having eight amino acids or less, typically seven or eight amino acids (e.g., amino acid residues). In some embodiments, the glycosylated Ang-(1-7) derivative is glycosylated with xylose, fucose, rhamnose, glucose, lactose, cellobiose, melibiose, or a combination thereof. Still in other embodiments, the carboxylic acid end of said glycosylated Ang-(1-7) derivative is substituted with an amino group.

Other aspects of the invention provide methods for treating cognitive dysfunction and/or impairment in a subject by administering a therapeutically effective amount of an oligonucleotide of the invention. In general, oligopeptides of the invention can be used to treat any clinical condition that can be treated with Ang-(1-7).

DETAILED DESCRIPTION OF THE INVENTION

Definitions

Figure 1:
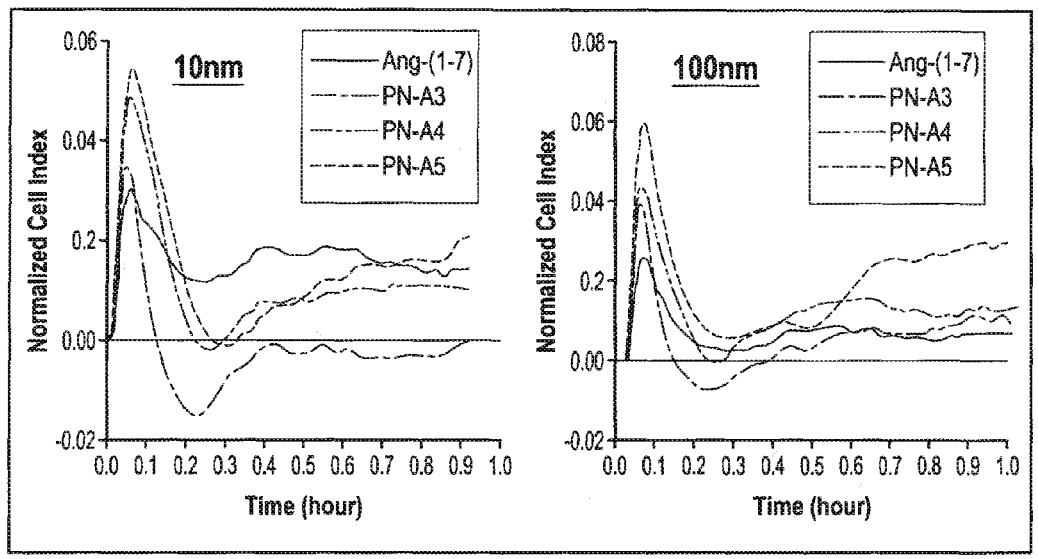
FIG. 1 is a graph showing some of the oligopeptides of the invention and native Ang-(1-7) to activate human umbilical vascular endothelial cells (HUVEC) in culture.

The term "native" refers to any sequence of L amino acids used as a starting sequence or a reference for the preparation of partial or complete retro, inverso or retro-inverso analogues. Thus, the term "native Ang-(1-7)" refers to an oligopeptide having the same amino acid sequence as that of endogenous Ang-(1-7). It should be appreciated that the use of the term "native" does NOT imply naturally occurring, although it can include naturally occurring Ang-(1-7). The term "native" merely refers to having the same amino acid sequence as that of Ang-(1-7) without any modification of the amino acid residues. Accordingly, the term "native Ang-(1-7)" includes both synthetic Ang-(1-7) and naturally occurring Ang-(1-7) as long as the amino acid residues are the same and are not modified.

The term "Ang-(1-7) derivative" refers to oligopeptide in which one or more amino acid residue is either modified or different than the amino acid residue of the corresponding native Ang-(1-7). The term "Ang-(1-7) derivative" also includes oligopeptide of eight amino acid residues as discussed in more detail below.

The term "retro modified" refers to a peptide which is made up of L-amino acids in which the amino acid residues are assembled in opposite direction to the native peptide with respect the which it is retro modified. The term "inverso modified" refers to a peptide which is made up of D-amino acids in which the amino acid residues are assembled in the same direction as the native peptide with respect to which it is inverso modified. The term "retro-inverso modified" refers to a peptide which is made up of D-amino acids in which the amino acid residues are assembled in the opposite direction to the native peptide with respect to which it is retro-inverso modified. Thus, native Ang-(1-7) (L-amino acids, N→C direction) is: Asp-Arg-Val-Tyr-Ile-His-Pro, i.e., DRVYIHP (SEQ ID NO:2). Retro-inverso Ang-(1-7) (D-amino acids, C→N direction) is: DRVYIHP (SEQ ID NO:3). Retro Ang-(1-7) (L-amino acids, C→N direction) is: DRVYIHP (SEQ ID NO:4). And inverso Ang-(1-7) (D-amino acids, N→C direction) is: DRVYIHP (SEQ ID NO:5). The use of D-amino acids in the context of inverso modified and retro-inverso modified Ang-(1-7) derivatives is not intended to be limiting on the use of D-amino amino acids in the oligopeptides. As discussed in more detail below, fewer than all of the amino acids in an Ang-(1-7) derivative may be D-amino acids.

The term "carbohydrate" refers to pentose and hexose of empirical formula $(CH_2O)_n$, where n is 5 for pentose and 6 for hexose. A carbohydrate can be monosaccharide, disaccharide, oligosaccharide (e.g., 3-20, typically 3-10, and often 3-5 monomeric saccharides are linked together), or polysaccharide (e.g., greater than 20 monomeric saccharide units). More often, the term carbohydrate refers to monosaccharide and/or disaccharide. However, it should be appreciated that the scope of the invention is not limited to mono- or di-saccharides. Often the terms "carbohydrate" and "saccharide" are used interchangeably herein.

The term "oligopeptide" as used throughout the specification and claims is to be understood to include amino acid chain of any length, but typically amino acid chain of about fifteen or less, often ten or less, still more often eight or less, and most often seven or eight.

It should be appreciated that one or more of the amino acids of Ang-(1-7) can be replaced with an "equivalent amino acid", for example, L (leucine) can be replaced with isoleucine or other hydrophobic side-chain amino acid such as alanine, valine, methionine, etc., and amino acids with polar uncharged side chain can be replaced with other polar uncharged side chain amino acids. While Ang-(1-7) comprises 7 amino acids, in some embodiments the oligopeptide of the invention has eight or less amino acids.

The term "derivative" refers to any chemical modification of the amino acid, such as alkylation (e.g., methylation or ethylation) of the amino group or the functional group on the side chain, removal of the side-chain functional group, addition of a functional group (e.g., hydroxyl group on proline), attachment of mono- or di-carbohydrate (e.g., via glycosylation) etc. Exemplary glycosylated derivatives include hydroxyl group on serine that is glycosylated with glucose, galactose, ribose, arabinose, xylose, lyxose, allose, altrose, mannose, gulose, iodose, talose, fucose, rhamnose, etc. as well as disaccharides and amino sugars such as galactosamine, glucosamine, sialic acid, N-acetyl glucosamine, etc. Amino acid derivatives also include modified or unmodified D-amino acids.

The term "combinations thereof," which reference to any modifications (e.g, carbohydrate modifications) of Ang-(1-7) derivatives refers to oligopeptides in which two, three, four, five, six, seven, or eight of the individual amino acids are modified by the attachment of a carbohydrate. For Ang-(1-7) derivatives having a plurality of carbohydrate modifications, the modifying carbohydrates may be the same on every modified amino acid, or the several modified amino acids may comprise a mixture of different carbohydrates.

"A therapeutically effective amount" means the amount of a compound that, when administered to a mammal, at an appropriate interval and for a sufficient duration for treating a disease, is sufficient to effect such treatment for the disease. The "therapeutically effective amount" will vary depending on the compound, the disease and its severity, physiological factors unique to the individual including, but not limited to the age, weight, and body mass index, the unitary dosage, cumulative dosage, frequency, duration, and route of administration selected.

As used herein, the term "treating", "contacting" or "reacting" when referring to chemical synthesis means to add or mix two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

As used herein, the terms "treating" and "treatment" refer to effecting an improvement of any symptom or physiological, cognitive, or biochemical indicium of the condition or disease being treated. For example, treatment of a cognitive dysfunction and/or impairment may refer to: (1) preventing cognitive dysfunction and/or impairment from occurring, i.e., causing the clinical symptoms of cognitive dysfunction and/or impairment not to develop in a subject that may be or predisposed to developing cognitive dysfunction and/or impairment but does not yet experience or display symptoms of cognitive dysfunction and/or impairment; (2) inhibiting cognitive dysfunction and/or impairment, i.e., arresting or reducing the development of cognitive dysfunction and/or impairment or its clinical symptoms; or (3) relieving cognitive dysfunction and/or impairment, i.e., causing regression of cognitive dysfunction and/or impairment or its clinical symptoms.

The terms "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value).

The term "subject" or "patient" refers to any organism to which a composition of this invention may be administered, e.g., for experimental, diagnostic, and/or therapeutic purposes. Typical subjects include animals (e.g., mammals such as mice, rats, rabbits, dogs, cats, non-human primates, and humans).

Unless defined otherwise, all technical and scientific terms used herein have the meaning commonly understood by a person skilled in the art to which this invention belongs.

Oligopeptides of the Invention: Some aspects of the invention provide oligopeptides that are derivatives of Ang-(1-7). As discussed above, the term "derivative" of Ang-(1-7) refers to an oligopeptide whose amino acid sequence of any one or more of Ang-(1-7) is modified (e.g., via methylation, presence of a functional group, such as hydroxy group on proline), attached to a carbohydrate, is replaced with corresponding D-amino acid or an "equivalent amino acid" as defined above, and/or the terminal amino group end or the carboxyl end of Ang-(1-7) is modified, for example, the carboxylic acid end can be modified to be an amide, an amine, a thiol, or an alcohol functional group, or one in which an additional amino acid residue is present compared to native Ang-(1-7). It should be appreciated that the term "Ang-(1-7) derivative" excludes the native Ang-(1-7), i.e., amino acid sequences of endogenous Ang-(1-7) without any modification.

In some embodiments, oligopeptides of the invention have the amino group on the carboxylic acid terminal end (i.e., the —OH group of the carboxylic acid is replaced with —NR$^a$R$^b$, where each of R$^a$ and R$^b$ is independently hydrogen or $C_1$-$C_6$ alkyl) and/or have one or more amino acid residues that are (i) replaced with a corresponding D-amino acid, (ii) glycosylated, (iii) replaced with another amino acid, (iv) or a combination thereof.

Still in other embodiments, the oligopeptide of the invention is retro-inverso Ang-(1-7). Yet in other embodiments, the oligopeptide of the invention is retro Ang-(1-7). In other embodiments, the oligopeptide of the invention is inverso Ang-(1-7).

Other embodiments of the invention include Ang-(1-7) derivatives in which at least one or more, typically one or two, and often only one amino acid is attached to a carbohydrate. Generally, the carbohydrate is attached to the amino acid via glycosylation. Typically, the carbohydrate is a mono- or di-carbohydrate. Exemplary mono- and di-carbohydrates that can be used in the invention include, but are not limited to, xylose, fucose, rhamnose, glucose, lactose, cellobiose, melibiose, and a combination thereof.

In one particular embodiment, the oligopeptide of the invention is Ang-(1-7) derivative of the formula: $A^1$-$A^2$-$A^3$-$A^4$-$A^5$-$A^6$-$A^7$-$A^8$ (SEQ ID NO:1), where $A^1$ is selected from the group consisting of aspartic acid, glutamic acid, alanine, and a derivative thereof; $A^2$ is selected from the group consisting of arginine, histidine, lysine, and a derivative thereof; $A^3$ is selected from the group consisting of valine, alanine, isoleucine, leucine, and a derivative thereof; $A^4$ is selected from the group consisting of tyrosine, phenylalanine, tryptophan, and a derivative thereof; $A^5$ is selected from the group consisting of isoleucine, valine, alanine, leucine, and as derivative thereof; $A^6$ is selected from the group consisting of histidine, arginine, lysine, and a derivative thereof; $A^7$ is selected from the group consisting of proline, glycine, serine, and a derivative thereof; and $A^8$ can be present or absent, wherein when $A^8$ is present, $A^8$ is selected from the group consisting of serine, threonine, hydroxyproline, and a derivative thereof, provided (i) at least one of $A^1$-$A^8$ is optionally substituted with a mono- or di-carbohydrate; or (ii) when $A^8$ is absent: (a) at least one of $A^1$-$A^7$ is substituted with a mono- or di-carbohydrate, (b) $A^7$ is terminated with an amino group, or (c) a combination thereof.

In some embodiments, $A^1$ is the amino terminal end of the oligopeptide and $A^8$ (or $A^7$ when $A^8$ is absent) is the carboxyl terminal end. Still in other embodiments, $A^1$ is the carboxyl terminal end and $A^8$ (or $A^7$ when $A^8$ is absent) is the amino terminal end. Yet in other embodiments, the carboxylic acid functional group of the carboxyl terminal end is modified as an amide functional group, an amine functional group, a hydroxyl functional group, or a thiol functional group. The amide and the amine functional groups can be non-alkylate, mono-alkylated or di-alkylated.

Yet in other embodiments, the carbohydrate comprises glucose, galactose, xylose, fucose, rhamnose, or a combination thereof. In some instances, the carbohydrate is a mono-carbohydrate, whereas in other instances, the carbohydrate is a di-carbohydrate.

In other embodiments, at least one of $A^1$-$A^8$ is substituted with a mono-carbohydrate. Still in other embodiments, at least one of $A^1$-$A^8$ is substituted with a di-carbohydrate. It should be appreciated that the scope of the invention also includes those oligopeptides having both mono- and di-carbohydrates.

Exemplary di-carbohydrates that can be used in oligopeptides of the invention include, but are not limited to, lactose, cellobiose, melibiose, and a combination thereof. However, it should be appreciated that the scope of the invention includes oligopeptides that are substituted with any dicarbohydrates known to one skilled in the art.

In one particular embodiment, $A^8$ is serine or a derivative thereof. In some instances, the carboxylic acid moiety of the serine is modified as an amide or an amine. In one case, serine is terminated as an amino group. Still in other embodiments, the serine residue of $A^8$ is glycosylated with glucose or lactose.

Yet in other embodiments, at least one, typically at least two, generally at least three, often at least four, still more often at least five, yet still more often at least six, and most often all of $A^1$-$A^8$ is D-amino acid.

In particular, in some specific embodiments, said oligopeptide is retro modified, inverso modified, or retro-inverso modified.

Another aspect of the invention provides oligopeptides, such as Ang-(1-7) derivatives, having eight amino acids or less, typically seven or eight amino acid residues. In some embodiments, one or more amino acids have attached thereto a carbohydrate group. Often the carbohydrate group is attached to the oligopeptide via glycosylation. The carbohydrate can be attached to the oligopeptide via any of the side chain functional group of the amino acid or the amide group. Accordingly, the scope of the invention includes, but is not limited to, O-glycosylate, N-glycosylate, S-glycosylated oligopeptides. The term "X-glycosylated" refers to having a carbohydrate attached to the oligopeptide via the heteroatom "X" of the amino acid. For example, for serine whose side-chain functional group is hydroxyl, "O-glycosylated" means the carbohydrate is attached to the serine's side-chain functional group, i.e., the hydroxyl group. Similarly, "N-glycosylation" of leucine refers to having the carbohydrate attached to the amino side-chain functional group of leucine. Typically, the glycosylation is on the side-chain functional group of the amino acid.

In some embodiments, the Ang-(1-7) derivative is glycosylated with xylose, fucose, rhamnose, glucose, lactose, cellobiose, melibiose, or a combination thereof.

Yet in other embodiments, the carboxylic acid terminal end of said glycosylated Ang-(1-7) derivative is substituted with an amino group. When referring to the carboxyl acid terminal end being substituted with an amino group, it means —OH group of the carboxylic acid is replaced with —NH$_2$ group. Thus, the actual terminal end functional group is an amide, i.e., rather than having the oligopeptide being terminated at the carboxylic acid terminal end with a functional group —CO$_2$H, the carboxylic acid terminal end is terminated with an amide group (i.e., —CO$_2$NR'$_2$, where each R' is independently hydrogen or $C_1$-$C_{12}$ alkyl). Still in other embodiments, the carboxylic acid terminal group is terminated with a hydroxyl or a thiol group. In some embodiments, the modified carboxylic acid terminal group is used to attach the carbohydrate, e.g., via glycosylation.

and, consequently, Mas activation, or intrinsic-efficacy. To improve (i.e., increase) penetration of the blood-brain barrier, in some embodiments the Ang-(1-7) derivative is attached to at least one mono- or di-carbohydrates.

Without being bound by any theory, it is believed that the oligopeptide of the invention that are glycosylated exploits the inherent amphipathicity of the folded Ang-(1-7) glycopeptides (i.e., glycosylated oligopeptides of the invention) and the "biousian approach" to deliver the glycosylated oligopeptides of the invention across the blood-brain barrier. In some instances, the amount of increase in crossing the blood-brain barrier by oligopeptides of the invention is at least 6%, typically at least 10%, and often at least 15% compared to native Ang-(1-7). In other instances, oligopeptides of the invention have in vivo half-life of at least 30 min, typically at least 40 min, and often at least 50 min. Alternatively, compared to native Ang-(1-7), oligopeptides of the invention exhibit at least 50 fold, typically at least 75 fold, and often at least 100 fold increase in in vivo half-life.

In other embodiments, oligopeptides of the invention exhibit enhanced vascular efficacy. Without being bound by any theory, it is generally recognized that blood-brain barrier transport occurs via an absorptive endocytosis process on the blood side of the endothelium of the brain capillaries followed by exocytosis on the brain side, leading to overall transcytosis. It is also believed that for this process to be efficient, the oligopeptide must bind to the membrane for some period of time, and must also be able to exist in the aqueous state for some period of time (biousian nature). Based on previous work from one of the present inventors, it is believed that effective drug delivery and blood-brain barrier transport requires a biousian glycopeptide that has at least two states: (1) a state defined, by one or more membrane-bound conformations that permit or promote endocytosis; and (2) a state defined by a water-soluble, or random coil state that permits "membrane hopping" and, presumably, vascular efficacy.

In general, the degree of glycosylation does not have a large effect on the structure of the individual microstates. Thus, altering the degree of glycosylation allows for the modulation of aqueous vs. membrane-bound state population densities without significantly affecting the overall structure of the oligopeptide. Moreover, it is believed that glycosylation also promotes stability to peptidases, thereby increasing the half-life of the Ang-(1-7) derivatives in vivo.

TABLE 1

Some of the representative oligopeptides of the invention.

|  | 1 | 2 | 3 | 4 | 5 | 6 | 7 | 8 | carboxyl terminal end functional group |
|---|---|---|---|---|---|---|---|---|---|
| Native AT$_{1-7}$ | Asp | Arg | Val | Tyr | Ile | His | Pro | — | OH (SEQ ID NO: 2) |
| PN-A1 | Asp | Arg | Val | Tyr | Ile | His | Pro | — | NH$_2$ (SEQ ID NO: 6) |
| PN-A2 | Asp | Arg | Val | Tyr | Ile | His | Pro | Ser° | NH$_2$ (SEQ ID NO: 7) |
| PN-A3 | Asp | Arg | Val | Tyr | Ile | His | Pro | Ser* | NH$_2$ (SEQ ID NO: 8) |
| PN-A4 | Asp | Arg | Val | Tyr | Ile | His | Pro | Ser** | NH$_2$ (SEQ ID NO: 9) |
| PN-A5 | Asp | Arg | Val | Tyr | Ile | His | Ser* | — | NH$_2$ (SEQ ID NO: 10) |
| PN-A6-PN-A11 | Ala | → | scan | Tyr | Ile | etc. | Pro | Ser°*/** | NH$_2$ (SEQ ID NO: 11) |
| PN-A12 | Asp | Arg | Xxx | Tyr | Yyy | His | Pro | Ser°*/** | NH$_2$ (SEQ ID NO: 12) |
| PN-AXX | Asp | Arg | Xxx | Zzz | Yyy | His | Pro | Ser°*/** | NH$_2$ (SEQ ID NO: 13) |

One of the purposes of the invention was to produce Ang-(1-7) derivatives to enhance efficacy of action, in vivo stabilization, and/or penetration of the blood-brain barrier. Improved penetration of the blood-brain barrier facilitates cerebral entry of the Ang-(1-7) derivative of the invention, Table 1 above shows some of the representative oligopeptides of the invention. In particular, these oligopeptides can be considered Ang-(1-7) derivatives. In Table 1, the "n-x", where x is an integer, represents the oligonucleotide identifier. For example, PN-A1 means oligopeptide number 1, PN-A2 means oligopeptide number 2, PN-A6-PN-A11 means oligopeptide numbers 6 through 11, and so forth. Thus, the term "A-x" is used for identification purposes only. As shown in Table 1, some of the oligopeptides have carbohydrate attached to the native Ang-(1-7) peptide. These peptides are sometimes referred to as glycopeptides.

Studies have shown that inherent binding of the glycopeptide to the native receptor is minimally affected. Therefore, the glycosylated Ang-(1-7) derivatives, at a minimum, maintain Mas binding similar to that of the native Ang-(1-7) peptide. In addition, promoting the aqueous nature of the glycopeptide can further enhance vascular efficacy of Ang-(1-7) derivatives. The degree of glycosylation (e.g., Table 1: unglycosylated Ser°, glycosylated Ser* or lactosylated Ser**) for optimal blood-brain barrier transport is determined using the best binding compounds from these using the in vivo mouse model. Besides the disaccharide β-lactose, the more robust disaccharide β-cellobiose is examined using these first few structures. Based on the amino acid sequence of Ang-(1-7) and the potential modification strategies, there are at least about 200 possible derivatives of Ang-(1-7) that are rapidly generated using the well known oligopeptide synthesis, including automated peptide synthesis as well as combinatorial synthesis.

Other aspects of the invention provide methods for treating cognitive dysfunction and/or impairment in a patient using an oligopeptide of the invention. Typically, methods of the invention include administering to a patient in need of such a treatment a therapeutically effective amount of an oligopeptide of the invention. It should be appreciated that the oligopeptides of the invention can be used to treat any clinical conditions that are known to be treatable or appears to be treatable using Ang-(1-7), However, for the sake or clarity and brevity, the invention will now be described in reference to treating cognitive dysfunction and/or impairment in a patient.

The cognitive dysfunction that occurs in congestive heart failure (CHF) patients includes decreased attention, memory loss, psychomotor slowing, and diminished executive function, all of which compromises patients' ability to comply with complex medical regimens, adhere to dietary restrictions and make self-care decisions. Mechanisms thought to contribute to cognitive impairment in patients with CHF include changes in cerebral blood flow, altered cerebrovascular autoregulation and microembolisms. In one study, cerebral blood flow was measured with single-photon emission computed tomography (SPECT) and found to be reduced by 30% in patients with severe heart failure. The causes for decreased cerebral perfusion in CHF have been attributed to low cardiac output, low blood pressure and altered cerebrovascular reactivity. In some cases, the cognitive impairment seen in CHF is improved following either heart transplant or improvement in cerebral blood flow via optimal management of CHF. However, for many patients with CHF, management is rarely optimal and the cognitive impairment persists. Interestingly, long-term follow up studies have revealed that cognitively normal CHF patients have a significantly higher risk of dementia or Alzheimer's disease compared to age-matched non-CHF controls, suggesting that CHF and cardiovascular disease predispose patients to further cognitive impairment and dementia.

During CHF, the well characterized, changes in the circulating neurochemical milieu and increases in inflammatory factors are also seen in the brain. Most of the studies on CHF-induced changes in inflammatory cytokines and ROS have focused on brain regions involved in sympathetic outflow regulation and not on cognition. CHF elevates sympathetic tone and causes abnormal cardiac and sympathetic reflex function. In the rat, ischemia-induced CHF significantly increases pro-inflammatory cytokines and Angiotensin II type 1 receptors (AT1) in the paraventricular nucleus (PVN) of the hypothalamus. Further, in CHF rabbits, the increase in sympathetic outflow is blocked by ICV injection of the super oxide dimustase (SOD) mimetic tempol, presumably by inhibition of ROS. CHF in this model is associated with increased expression of NADPH oxidase subunits and ROS production in the rostral ventral lateral medulla (RVLM) and increases in NO.

The role of ROS in learning and memory has been extensively studied. All of the NAD(P)H oxidase subunits, including NOX2 and NOX4, have been localized within the cell bodies and dendrites of neurons of the mouse hippocampus and perirhinal cortex and are co-localized at synaptic sites. These are key regions of the brain in learning and memory. In the brain, superoxide production via actions of NAD(P)H oxidase are known to be involved in neurotoxicity, age related dementia, stroke and neurodegenerative diseases and have been identified throughout the brain including the hippocampus, thalamus, cerebellum and amygdala. In younger, healthy animals ROS and NAD(P)H oxidase is shown to be required for normal learning and hippocampal long-term potentiation (LTP). Recent studies in mice lacking Mas have shown that Ang-(1-7) and Mas are essential for normal object recognition processing and blockade of Mas in the hippocampus impairs object recognition. In addition, Ang-(1-7) facilitates LTP in CA1 cells and this effect is blocked by antagonism of Mas. In older animals or in CHF animals, an increase in ROS is linked to LTP and memory impairments.

Over the last decade, it has become recognized that renin angiotensin system (RAS) involves two separate enzymatic pathways providing a physiological counterbalance of two related peptides acting at distinct receptors. The well described ACE-AngII-AT1 receptor system is thought to be physiologically opposed and balanced by the ACE2-Ang-(1-7)-Mas system. Functionally, these two separate enzymatic pathways of RAS are thought to be involved in balancing ROS production and nitric oxide (NO) in the brain, microvasculature and peripheral tissues. Increases in AT1 receptor activation are known to increase NAD(P)H oxidase and ROS generation which are both known to contribute to abnormal increases of sympathetic nerve activity observed in CHF and hypertension. This increase in AT1 receptor-induced ROS formation is thought to be opposed by ACE2-Ang-(1-7)-Mas inhibition of ROS formation. Ang-(1-7), the majority of which is produced from ACE2 cleavage of Ang II, decreases ROS production and increases NOS in the brain via activation Mas and, possibly through AT2 receptor.

Within the brain, the Mas receptor is known to be expressed on neurons, microglia and vascular endothelial cells. Further, all three of these key components that make up the "neurovascular unit" (neurons, microglia and endothelial cells) are central players in neurogenic hypertension and CHF-induced increases in brain inflammation and ROS production. Both CHF and hypertension increase circulating cytokines promoting ROS production within the "neurovascular unit". The end-result of this feed-forward cascade is neuronal dysfunction and cognitive impairment. The ideal therapeutic candidate to treat cognitive impairment would be designed to interrupt this cascade by working at both sides of the blood-brain barrier, the brain vascular endothelium and neuronal cells. Ang-(1-7), acting at the Mas receptor, is known to have effects at both endothelial cells and neurons. However, using a native Ang-(1-7) for treating cognitive dysfunction and/or impairment is not suitable because native Ang-(1-7) is susceptible to enzymatic degradation. Moreover, native Ang-(1-7) does not readily cross the blood-brain barrier to be suitable as a therapeutic agent.

Without being bound by any theory, it is believed that one of the advantages of using oligopeptides of the invention in treating cognitive dysfunction and/or impairment is that oligopeptides of the invention have enhanced endothelial "interaction" and brain penetration. It is believed that oligopeptides of the invention act at both endothelial cells and neurons thus inhibiting inter alia neurovascular ROS production and mitigating the brain inflammatory cascade.

Accordingly, oligopeptides the invention can be used to treat cognitive impairment and/or dysfunction (1) associated with pre- and/or post-surgery dementia, or (2) observed in patients with congestive heart failure, cardiovascular disease, or hypertension. More generally, oligopeptides of the invention are useful in treating cognitive dysfunction and/or impairment in a subject whose cognitive dysfunction and/or impairment is clinically associated with an increase in inflammatory cytokines and/or increase in reactive oxygen species ("ROS") in the central nervous system, in particular the brain. As used herein, the term "clinically associated" refers to the root cause or underlying cause of cognitive dysfunction and/or impairment (such as, but not limited to, memory loss) that when ameliorated results in reduction, prevention, treatment or reversal of cognitive dysfunction and/or impairment. Exemplary clinical conditions associated with an increase in inflammatory cytokines and/or increase in reactive oxygen species that can cause cognitive dysfunction and/or impairment include, but are not limited to, circulatory compromise, cardiovascular disease, hypertension, hypotension, congestive heart failure, stroke, embolism, surgery (e.g., postoperative recovery condition), dementia, Alzheimer's disease, disease related cognitive impairment, trauma related cognitive impairment, age-related dementia, postoperative related delirium and/or increase in inflammatory cytokine and/or increase in reactive oxygen species within the central nervous system of said subject or a combination thereof.

Oligopeptides of the present invention can be administered to a patient to achieve a desired physiological effect. Preferably the patient is an animal, more preferably a mammal, and most preferably a human. The oligopeptide can be administered in a variety of forms adapted to the chosen route of administration, i.e., orally or parenterally. Parenteral administration in this respect includes administration by the following routes: intravenous; intramuscular; subcutaneous; intraocular; intrasynovial; transepithelially including transdermal, ophthalmic, sublingual and buccal; topically including ophthalmic, dermal, ocular, rectal and nasal inhalation via insufflation and aerosol; intraperitoneal; and rectal systemic.

The active oligopeptide can be orally administered, for example, with an inert diluent or with an assimilable edible carrier, or it can be enclosed in hard or soft shell gelatin capsules, or it can be compressed into tablets. For oral therapeutic administration, the active oligopeptide may be incorporated with excipient and used in the form of ingestible tablets, buccal tablets, troches, capsules, elixirs, suspensions, syrups, wafers, and the like. Such compositions and preparation can contain at least 0.1% of active oligopeptide. The percentage of the compositions and preparation can, of course, be varied and can conveniently be between about 1 to about 10% of the weight of the unit. The amount of active oligopeptide in such therapeutically useful compositions is such that a suitable dosage will be obtained. Preferred compositions or preparations according to the present invention are prepared such that an oral dosage unit form contains from about 1 to about 1000 mg of active oligopeptide.

The tablets, troches, pills, capsules and the like can also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin can be added or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the active oligopeptide, sucrose as a sweetening agent, methyl and propylparabens a preservatives, a dye and flavoring such as cherry or orange flavor. Of course, any material used in preparing any dosage unit form should be pharmaceutically pure and substantially non-toxic in the amounts employed. In addition, the active oligopeptide can be incorporated into sustained-release preparations and formulation.

The active oligopeptide can also be administered parenterally. Solutions of the active oligopeptide can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It can be stable under the conditions of manufacture and storage and must be preserved against the contaminating action of microorganisms such as bacterial and fungi. The carrier can be a solvent of dispersion medium containing, for example, water, ethanol, polyol (e.g., glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, e.g., sugars or sodium chloride. Prolonged absorption of the injectable compositions of agents delaying absorption, e.g., aluminum monostearate and gelatin.

Sterile injectable solutions are prepared by incorporating the active oligopeptide in the required amount in the appropriate solvent with various other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic oligopeptides of the present invention can be administered to a mammal alone or in combination with pharmaceutically acceptable carriers, as noted above, the proportion of which is determined by the solubility and chemical nature of the oligopeptide, chosen route of administration and standard pharmaceutical practice.

The physician will determine the dosage of the present therapeutic agents which will be most suitable for prophylaxis or treatment and it will vary with the form of administration and the particular oligopeptide chosen, and also, it will vary with the particular patient under treatment. The physician will generally wish to initiate treatment with small dosages by small increments until the optimum effect under the circumstances is reached. The therapeutic dosage can generally be from about 0.1 to about 1000 mg/day, and preferably from about 10 to about 100 mg/day, or from about 0.1 to about 50 mg/Kg of body weight per day and preferably from about 0.1 to about 20 mg/Kg of body weight per day and can be administered in several different dosage units. Higher dosages, on the order of about 2× to about 4×, may be required for oral administration.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Ang-(1-7) Derivative High-Throughput Screening (HTS): For HTS, a sensitive and direct measure of nitric oxide (NO) production in 2 separate cell lines is utilized, primary CA1 hippocampal neurons and human umbilical vein endothelial cells (HUVEC). The use of primary CA1 cells is self-evident for the study of central effects. In addition, the contribution of endothelial dysfunction to the progression of CHF and to the induction of cognitive impairment is clinically appreciated. The emerging picture that the Ang-(1-7) singling axis holds promise as a therapeutic target for endothelial dysfunction strongly indicates that reversal of CHF-induced endothelial dysfunction as mechanism cannot be ruled out. HUVEC are isolated from the human umbilical vein and cryo-preserved after primary culture. HUVEC is included as a second line for the primary screen because these cells are the model in vitro system for the study of endothelial cell function and can be used to directly measure Mas-dependent NO production.

Cell Culture. To isolate primary hippocampal CA1 neuronal cells, whole brain was removed from neonatal rat pups (1-2 day old) and the cortices dissected away. The hippocampus was isolated and the CA1 field was excised and placed in buffer. After gentle disruption in digestion buffer, the cells were counted, placed in culture media, and plated in a 96-well format coated with poly-d-lysine. At the time of plating, cells were approximately at 50% density and were allowed to culture to 70-80% density before starting the assay. Commercially available HUVEC (Life Technologies/Thermo Fisher) was thawed and plated (5000-10,000 cells/well) in a 96-well format coated with gelatin. HUVEC cells were allowed to culture overnight before starting the assay.

Cell Activation: The xCELLigence system Real-Time Cell Analyzer (RTCA), developed by Roche Applied Science, uses microelectronic biosensor technology to do dynamic, real-time, label-free, and non-invasive analysis of cellular events including G-protein receptor activation of cells. The RTCA analysis was utilized to measure the potency and relative ability of oligopeptides of the invention and native Ang-(1-7) to activate human umbilical vascular endothelial cells (HUVEC) in culture. Following uniform cellular adherence based on a linear increase in cell impedance (CI), HUVECs were treated with Ang-(1-7) and oligopeptides of the invention. Each trace of the CI over time in FIG. 1 represents the average of 4 wells normalized to CI at the time of compound addition. FIG. 1 shows the results from data acquired using the xCELLigence RTCA to measure the relative potency of PN-A3, PN-A4, PN-A5 and native Ang-(1-7). A 100 nM administration of PN-A3, PN-A4 and PN-A5 and 10 nM of PN-A3 and PN-A5 resulted in a significant (~2-fold) increase in CI over the native Ang-(1-7) demonstrating that the oligopeptides of the invention have greater potency for cell activation than native Ang-(1-7).

NO Production Assay. As a screen for mechanisms of action of oligopeptides of the invention, the ability to increase NO production of three oligopeptides of the invention (PN-A3, PN-A4 and PN-A5) were characterized and compared to native Ang-(1-7). Human umbilical vascular endothelial cells (HUVEC) culture plates received fluorescence reaction buffer (0.2 M phosphate buffer, pH 7, 1 mM EDTA, 0.1% glucose) containing diaminofluorescein-FM diacetate (DAF-FM, 1 µM) to measure real-time NO production. Time-resolved (10 minutes) fluorescent intensity was detected using a BioTek Synergy 2 microplate reader with excitation at 485 nm and emission at 535 nm. DAF-FM is a sensitive fluorometric derivative for the selective detection of NO in live cells.

Figure 2:
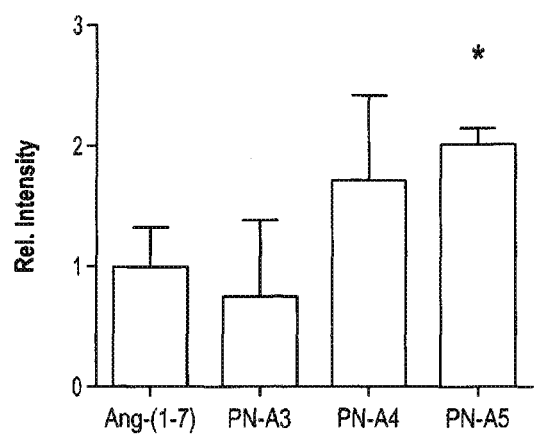
FIG. 2 is a graph showing NO production assay results for native Ang-(1-7) and oligopeptides PN-A3, PN-A4 and PN-A5 of the invention.

FIG. 2 shows relative peak fluorescence intensity following 5 minutes exposure to native Ang-(1-7) and three oligopeptides of the invention. Values were normalized to control fluorescence. As expected, native Ang-(1-7) induced a significant elevation of NO over control levels. More importantly, as shown in FIG. 2, oligopeptides of the invention (namely PN-A3, PN-A4 and PN-A5) also elicited a significant elevation of NO over control levels, with PN-A5 significantly enhancing NO production over that seen with native Ang-(1-7), *=p<0.05. These results demonstrate that oligopeptides of the invention increase NO production similar to or greater than that of native Ang-(1-7).

Figure 3A:
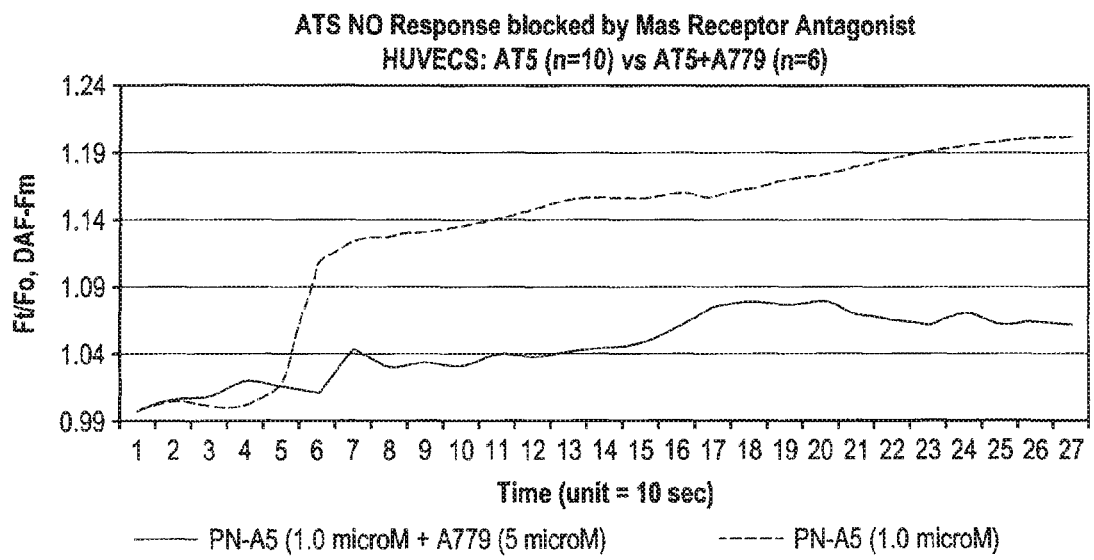
FIG. 3A is a graph showing the select Mas receptor antagonists A779 blocks NO production induced by oligopeptide PN-A5 of the invention.

FIG. 3A illustrates the ability of the select Mas receptor antagonists, A779, ($C_{39}H_{60}N_{12}O_{11}$) which is known to block native Ang-(1-7) NO production, to also block NO production induced by the oligopeptide of the invention, namely PN-A5. In these studies, HUVEC cells were incubated with DAF-FM, 1 µM to measure real-time NO production. Cells were treated with either PN-A5 alone (1.0 mM, n=10), PN-A5+A779 (n=6). Measurements were obtained using an Olympus 550 Confocal Microscope and analyzed using Image J. Images were obtained every 10 sec. These results indicate that the oligopeptide PN-A5 actions are due to activation of the Mas receptor.

Figure 3B:
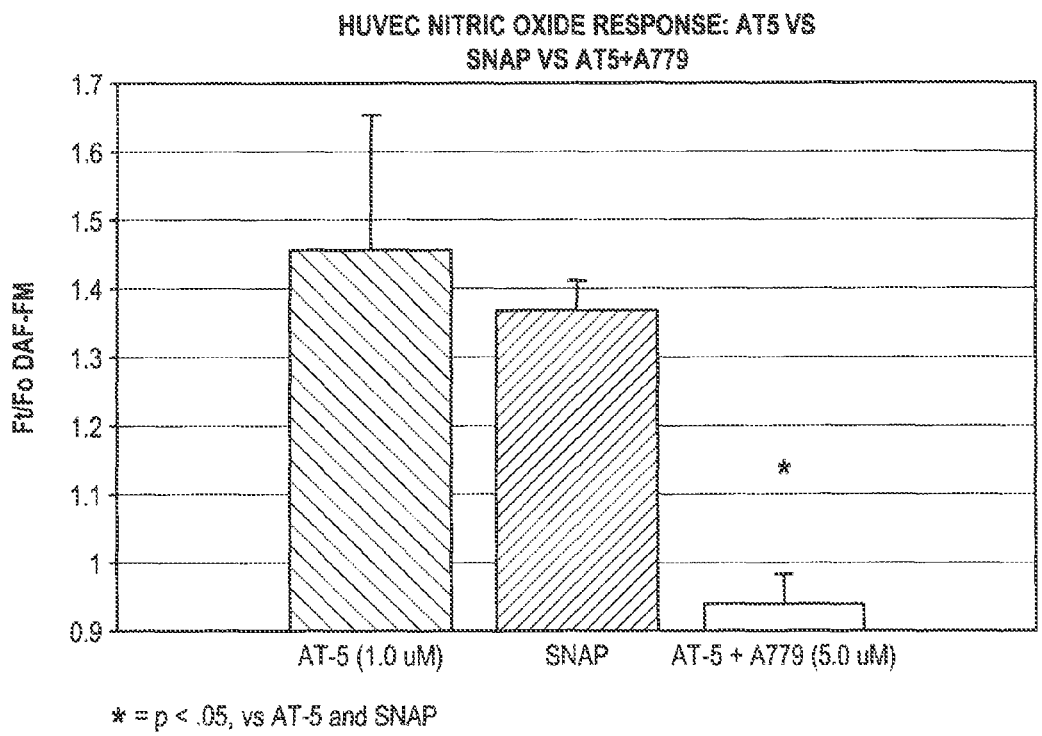
FIG. 3B is a graph showing the averaged effect of the select Mas receptor antagonists A779 on NO production induced by oligopeptide PN-A5.

FIG. 3b shows the averaged effect of the select Mas receptor antagonists, A779, which is known to block native Ang-(1-7) NO production, to also block NO production induced by the oligopeptide of the invention, PN-A5. In these studies, HUVEC cells were incubated with DAF-FM, 1 µM to measure real-time NO production. Cells were treated with either PN-A5 alone (1.0 mM, PN-A5+A779 (n=6), or the NO donor S-nitroso-N-acetylpenicillamine (SNAP). Fluorescent measurements were obtained using an Olympus 550 Confocal Microscope and analyzed using Image J. Images were obtained every 10 sec. The NO response produced by PN-A5 was completely blocked by A779 demonstrating that PN-A5's ability to increase NO is due to PN-A5 actions on the Mas receptor.

Effects of Ang-(1-7) Derivative on Heart Failure (HF) Induced Cognitive Impairment: A total of 33, male C57Bl/6J adult mice (Harlan, 8-10 weeks old) were used. Mice were randomly assigned to either the sham (n=12) or congestive heart failure (CHF) group (n=21). Experimental groups are described as follows: sham+saline, CHF+saline, CHF+PN-A5. All mice prior to surgery were weighed and anesthetized. For the CHF mice, MI was induced by ligation of the left coronary artery (LCA). Under anesthesia (2.5% isoflurane in a mixture of air and $O_2$) a thoracotomy was performed at the fourth left intercostal space and the LCA permanently ligated to induce a myocardial infarction (MI). Occlusion of the LCA was confirmed by observing blanching, a slight change in color of the anterior wall of the left ventricle downstream of the ligature. Sham mice underwent the same procedure with the exception of ligating the LCA.

Following 8 weeks post MI surgery, CHF mice were treated with either daily subcutaneous injections of the Ang-(1-7) derivative PN-A5 (1 mg/kg/day) for 28 days or saline. After 21 days, animals were tested for object recognition using a standard NOR test as described below. After approximately 25 days of treatment, animals were tested for spatial memory using the standard Morris water task as described below.

Novel Object Recognition (NOR): The apparatus consisted of an evenly illuminated Plexiglas box (12 cm×12 cm×12 cm) placed on a table inside an isolated observation room. All walls of the apparatus were covered in black plastic, and the floor was grey with a grid that was used to ensure that the location of objects did not change between object familiarization and test phases. The mouse behavior and exploration of objects was recorded with a digital camera. The digital image from the camera was fed into a computer in the adjacent room. Two digital stopwatches were used to track the time the mouse spent interacting with the objects of the test. All data was downloaded to Excel files for analysis. Triplicate sets of distinctly different objects were used for the test.

The novel object recognition task included 3 phases: habituation phase, familiarization phase, and test phase. For the habituation phase, on the first and second day, mice were brought to the observation room habituated to the empty box for 10 min per day. On the third day, each mouse had a "familiarization" trial with two identical objects followed by a predetermined delay period and then a "test" trial in which one object was identical to the one in the familiarization phase, and the other was novel. All stimuli were available in triplicate copies of each other so that no object needed to be presented twice. Objects were made of glass, plastic or wood that varied in shape, color, and size. Therefore, different sets of objects were texturally and visually unique. Each mouse was placed into the box the same way for each phase, facing the center of the wall opposite to the objects. To preclude the existence of olfactory cues, the entire box and objects were always thoroughly cleaned with 70% ethanol after each trial and between mice. During the familiarization phase, mice were allowed to explore the two identical objects for 4 min and then returned to their home cages. After a 2 hour delay, the "test phase" commenced. The mice were placed back to the same box, where one of the two identical objects presented in the familiarization phase was switched to a novel one and the mouse was allowed to explore these objects for another 4 min. Mouse "exploratory behavior" was defined as the animal directing its nose toward the object at a distance of ~2 cm or less. Any other behavior, such as resting against the object, or rearing on the object was not considered to be exploration. Exploration was scored by an observer blind to the mouse's surgical group (CHF vs. Sham). Finally, the positions of the objects in the test phases, and the objects used as novel or familiar, were counterbalanced between the 2 groups of mice.

Discrimination ratios were calculated from the time spent exploring the novel object minus time spent exploring the familiar object during the test phase divided by the total exploration time. DRatio=(t novel−t familiar)/(t novel+t familiar). Data were analyzed from first 2 minutes of 'test phase'. A positive score indicates more time spent with the novel object, a negative score indicates more time spent with the familiar object, and a zero score indicates a null preference. All NOR data was examined using one-way analysis of variance, between subjects (ANOVA). Individual group differences were tested using the post hoc Tukey HSD test. In comparisons between groups of different sample sizes, equal variance was tested using a modified Levene's test. All statistical tests and p-values were calculated using MS Excel with Daniel's XLtoolbox and alpha was set at the 0.05 level. Error bars represent SEM.

Morris Water Task: Testing Spatial Learning and Memory/Visual Test: The apparatus used was a large circular pool approximately 1.5 meters in diameter, containing water at 25° C. made opaque with addition of non-toxic white Crayola paint. An escape platform was hidden just below the surface of the water. Visual, high contrast cues were placed on the walls of the test room. A digital camera connected to a computer in the adjacent room is suspended over the tank to record task progress. For spatial testing prior to MI at 4 and 8 weeks post-MI or sham surgery, the platform was located at different sites in the pool.

During the spatial version of the Morris water task, all animals were given 6 training trials per day over 4 consecutive days. During these trials, an escape platform was hidden below the surface of water. Mice were released from seven different start locations around the perimeter of the tank, and each animal performed two successive trials before the next mouse was tested. The order of the release locations was pseudo-randomized for each mouse such that no mouse was released from the same location on two consecutive trials. Performance on the swim task was analyzed with a commercial software application (ANY-maze, Wood Dale, Ill.). Because different release locations and differences in swimming velocity produce variability in the latency to reach the escape platform, a corrected integrated path length (CIPL) was calculated to ensure comparability of mice performance across different release locations. The CIPL value measures the cumulative distance over time from the escape platform corrected by an animal's swimming velocity, and is equivalent to the cumulative search error. Therefore, regardless of the release location, if the mouse mostly swims towards the escape platform the CIPL value will be low. In contrast, the more time a mouse spends swimming in directions away from the platform, the higher the CIPL value.

Figure 4:
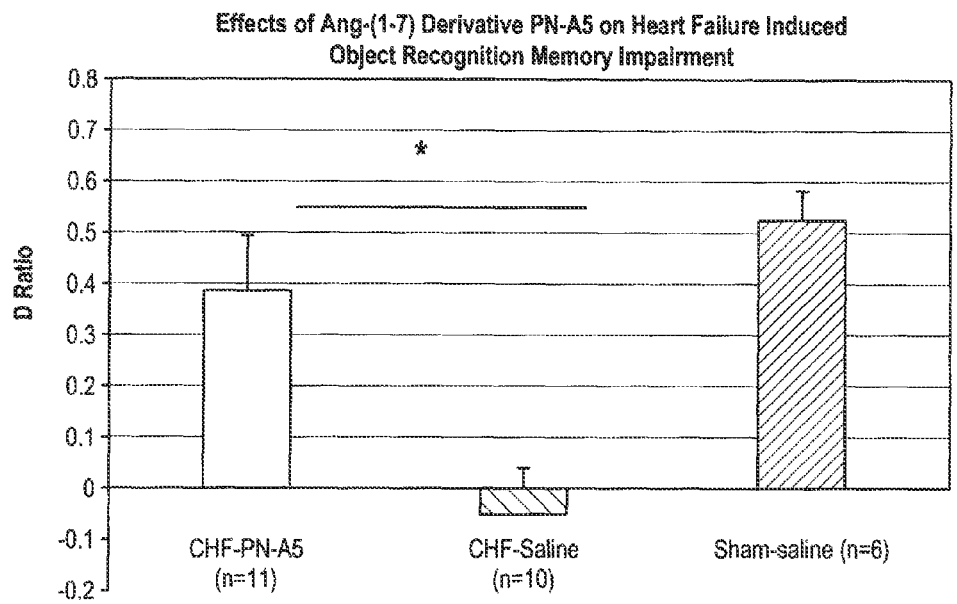
FIG. 4 is a graph showing the effects of oligopeptide PN-A5 on heart failure induced object recognition memory impairment.

Following approximately 21 days of treatment with oligopeptide PN-A5, CHF mice showed object recognition memory improvement. FIG. 4 illustrates the effects of three weeks treatment with oligopeptide PN-A5 on object recognition memory as determined by the Novel Object Recognition Test (NOR). The mean performance of CHF mice with oligopeptide PN-A5 treatment (n=11) was similar to sham mice with saline (n=6), (CHF-Ang-(1-7) derivative PN-A5 M=+0.38, SE 0.11 vs. Sham-saline M=+0.52, SE 0.06) and significantly greater in comparison to CHF mice treated with saline (n=10) (M=−0.05, SE 0.09, *=p=0.009. These results demonstrate that oligopeptide PN-A5 acts to attenuate and even rescue object recognition memory impairment in mice with CHF.

Figure 5:
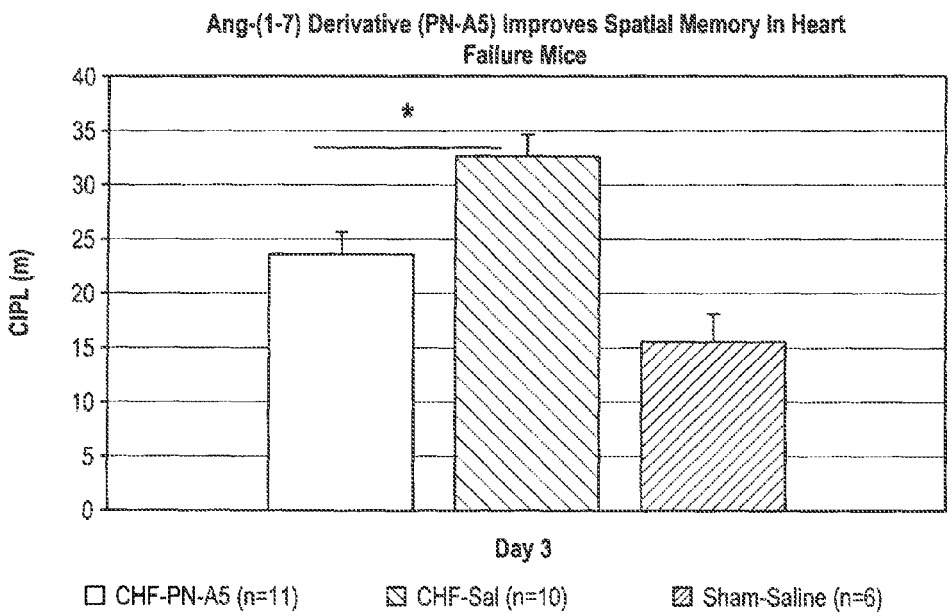
FIG. 5 is a graph showing the effects of oligopeptide PN-A5 on heart failure induced spatial memory impairment.

Following approximately 25 days of treatment with oligopeptide PN-A5, CHF mice showed spatial memory improvement. FIG. 5 shows the mean CIPL of CHF+ oligopeptide PN-A5 mice (n=11), CHF-saline treated mice (n=10) and Sham+saline mice (n=6). The CHF+oligopeptide PN-A5 mice showed significant improvement in spatial memory day 3 of the Morris swim task as compared to CHF-saline mice. CHF mice treated with saline had a significantly higher CIPL score as compared to CHF-oligopeptide PN-A5 treated mice (CHF-saline M=32.5, SE=2.1 vs CHF-oligopeptide PN-A5 M=23.5, SE 2.2, *=p=0.003. These results demonstrate that oligopeptide PN-A5 improves spatial memory.

Effect of Oligopeptide PN-A5 on Nitric Oxide Bone Pain: Female BALB/cfC3H mice (Harlan, Ind., USA) were 15 to 20 g prior to initiation of study (n 5 animals per treatment group). Clinical signs of morbidity were monitored and mice not meeting inclusion parameters (e.g. paralysis, rapid weight loss of >20% in 1 week) were removed from the study.

Mice were anesthetized with ketamine:xylazine (80 mg:12 mg/kg, 10 ml/kg injection volume; Sigma-Aldrich). An arthrotomy was performed. The condyles of the right distal femoris were exposed and a hole was drilled to create a space for injection of $4 \times 10^4$ 66.1 cells in 5 µL Opti-MEM or 5 µL Opti-MEM without cells in control animals within the intramedullary space of the mouse femoris. Injections were made with an injection cannula affixed via plastic tubing to a 10-µL Hamilton syringe (CI31, Plastics One). Proper placement of the injector was confirmed through use of Faxitron X-ray imaging. Holes were sealed with bone cement.

Spontaneous pain (flinching and guarding), and tactile allodynia were measured 0, 15, 30, 60, 90 and 120 minutes after a single dose of drug was administered in a blinded fashion on Day 7. Breast cancer-induced hypersensitivity returned to baseline levels 2 hours after drug administration. Flinching and guarding were observed for duration of 2 minutes during a resting state. Flinching was characterized by the lifting and rapid flexing of the right hind paw when not associated with walking or movement. Flinches were recorded on a five-channel counter. Guarding was characterized by the lifting the right hind limb into a fully retracted position under the torso. Time spent guarding over the duration of 2 minutes was recorded.

The assessment of tactile allodynia consisted of measuring the withdrawal threshold of the paw ipsilateral to the site of tumor inoculation in response to probing with a series of calibrated von Frey filaments using the Chaplan up-down method with the experimenter blinded to treatment groups. The 50% paw withdrawal threshold was determined by the nonparametric method of Dixon.

On day 7, mice received an intraperitoneal (i.p.) injection of either saline or 0.8 µg/µL (200 µL) for a total dose of 800 µg/kg. The in-vivo efficacy of PN-A5 was measured for a total of 2 hours.

Within group data were analyzed by non-parametric one-way analysis of variance. Differences were considered to be significant if P≤0.05. All data were plotted in GraphPad Prism 6.

Figure 6A:
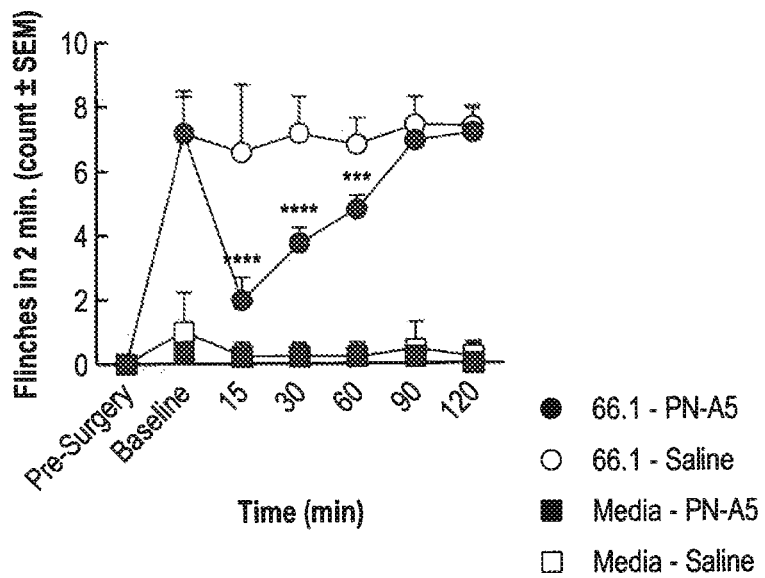
FIG. 6A is a graph showing oligopeptide PN-A5 attenuates CIBP acutely.
Figure 6B:
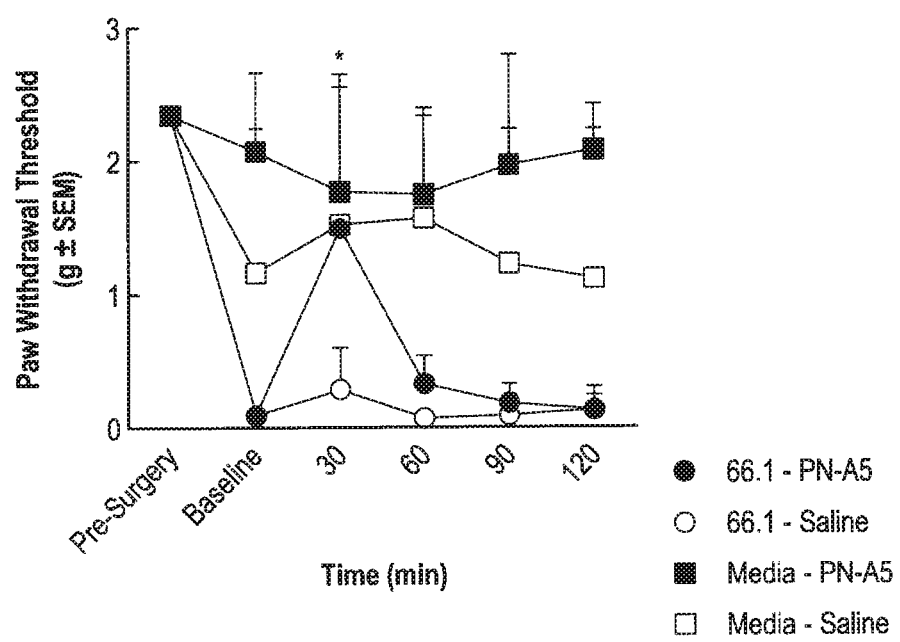
FIG. 6B is a graph showing the results of tactile allodynia test using von Frey filaments.

FIG. 6 shows the results on the effects of oligopeptide PN-A5 on cancer induced bone pain (CIBP). Cancer implanted into the distal femoralis of mice induced a significant increase in the number of spontaneous flinches (FIG. 6A) and time spent guarding (FIG. 6B) after 7 days. Administration of a bolus of PN-A5 (800 µg/kg, i.p.) significantly reversed cancer induces spontaneous pain for nearly one hour in duration (flinching: 60 min; guarding: 30 min; p<0.001). Similarly, cancer-induced tactile hypersensitivity was significantly attenuated 30 minutes after injection (p<0.01). For all measurements, the time of peak effect was 15-30 min. Behaviors returned to post-surgery values 90 min post-injection. Media inoculated, sham control animals did were not statistically different from pre-surgery baselines at any point during time-course.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

SEQUENCE LISTING

```
<160> NUMBER OF SEQ ID NOS: 13

<210> SEQ ID NO 1
<211> LENGTH: 8
<212> TYPE: PRT
<213> ORGANISM: Artificial Sequence
<220> FEATURE:
<223> OTHER INFORMATION: Artificial Construct
<220> FEATURE:
<221> NAME/KEY: MISC_FEATURE
<222> LOCATION: (1)..(1)
<223> OTHER INFORMATION: aspartic acid, glutamic acid, alanine or a
      derivative thereof.
<220> FEATURE:
<221> NAME/KEY: MISC_FEATURE
<222> LOCATION: (2)..(2)
```

```
<223> OTHER INFORMATION: arginine, histidine, lysine, or a derivative
      thereof
<220> FEATURE:
<221> NAME/KEY: MISC_FEATURE
<222> LOCATION: (3)..(3)
<223> OTHER INFORMATION: valine, alanine, isoleucine, leucine, or a
      derivative thereof.
<220> FEATURE:
<221> NAME/KEY: MISC_FEATURE
<222> LOCATION: (4)..(4)
<223> OTHER INFORMATION: tyrosine, phenylalanine, tryptophan, or a
      derivative thereof.
<220> FEATURE:
<221> NAME/KEY: MISC_FEATURE
<222> LOCATION: (5)..(5)
<223> OTHER INFORMATION: isoleucine, valine, alanine, leucine, or a
      derivative thereof.
<220> FEATURE:
<221> NAME/KEY: MISC_FEATURE
<222> LOCATION: (6)..(6)
<223> OTHER INFORMATION: histidine, arginine, lysine, or a derivative
      thereof.
<220> FEATURE:
<221> NAME/KEY: MISC_FEATURE
<222> LOCATION: (7)..(7)
<223> OTHER INFORMATION: proline, glycine, serine, or a derivative
      thereof.
<220> FEATURE:
<221> NAME/KEY: MISC_FEATURE
<222> LOCATION: (8)..(8)
<223> OTHER INFORMATION: can be absent or is serine, threonine,
      hydroxyproline, or a derivative thereof

<400> SEQUENCE: 1

Xaa Xaa Xaa Xaa Xaa Xaa Xaa Xaa
1               5

<210> SEQ ID NO 2
<211> LENGTH: 7
<212> TYPE: PRT
<213> ORGANISM: Homo sapiens

<400> SEQUENCE: 2

Asp Arg Val Tyr Ile His Pro
1               5

<210> SEQ ID NO 3
<211> LENGTH: 7
<212> TYPE: PRT
<213> ORGANISM: Artificial Sequence
<220> FEATURE:
<223> OTHER INFORMATION: Artificial Construct
<220> FEATURE:
<221> NAME/KEY: MISC_FEATURE
<222> LOCATION: (1)..(7)
<223> OTHER INFORMATION: D-amino acids in C to N direction

<400> SEQUENCE: 3

Asp Arg Val Tyr Ile His Pro
1               5

<210> SEQ ID NO 4
<211> LENGTH: 7
<212> TYPE: PRT
<213> ORGANISM: Artificial Sequence
<220> FEATURE:
<223> OTHER INFORMATION: Artificial Construct
<220> FEATURE:
<221> NAME/KEY: MISC_FEATURE
<222> LOCATION: (1)..(7)
<223> OTHER INFORMATION: L-amino acids in C to N direction

<400> SEQUENCE: 4
```

Asp Arg Val Tyr Ile His Pro
1               5

<210> SEQ ID NO 5
<211> LENGTH: 7
<212> TYPE: PRT
<213> ORGANISM: Artificial Sequence
<220> FEATURE:
<223> OTHER INFORMATION: Artificial Construct
<220> FEATURE:
<221> NAME/KEY: MISC_FEATURE
<222> LOCATION: (1)..(7)
<223> OTHER INFORMATION: D-amino acids from N to C direction

<400> SEQUENCE: 5

Asp Arg Val Tyr Ile His Pro
1               5

<210> SEQ ID NO 6
<211> LENGTH: 7
<212> TYPE: PRT
<213> ORGANISM: Artificial Sequence
<220> FEATURE:
<223> OTHER INFORMATION: Artificial Construct
<220> FEATURE:
<221> NAME/KEY: MISC_FEATURE
<222> LOCATION: (7)..(7)
<223> OTHER INFORMATION: -OH of carboxylic acid terminal group is
      replaced with -NH2 group.

<400> SEQUENCE: 6

Asp Arg Val Tyr Ile His Pro
1               5

<210> SEQ ID NO 7
<211> LENGTH: 8
<212> TYPE: PRT
<213> ORGANISM: Artificial Sequence
<220> FEATURE:
<223> OTHER INFORMATION: Artificial Construct
<220> FEATURE:
<221> NAME/KEY: MISC_FEATURE
<222> LOCATION: (8)..(8)
<223> OTHER INFORMATION: -OH of the carboxylic acid terminal is replaced
      with -NH2

<400> SEQUENCE: 7

Asp Arg Val Tyr Ile His Pro Ser
1               5

<210> SEQ ID NO 8
<211> LENGTH: 8
<212> TYPE: PRT
<213> ORGANISM: Artificial Sequence
<220> FEATURE:
<223> OTHER INFORMATION: Artificial Construct
<220> FEATURE:
<221> NAME/KEY: MISC_FEATURE
<222> LOCATION: (8)..(8)
<223> OTHER INFORMATION: Glucosylated and -OH of the carboxylic acid
      terminal end is replaced with -NH2.

<400> SEQUENCE: 8

Asp Arg Val Tyr Ile His Pro Ser
1               5

<210> SEQ ID NO 9
<211> LENGTH: 8
<212> TYPE: PRT

```
<213> ORGANISM: Artificial Sequence
<220> FEATURE:
<223> OTHER INFORMATION: Artificial Construct
<220> FEATURE:
<221> NAME/KEY: MISC_FEATURE
<222> LOCATION: (8)..(8)
<223> OTHER INFORMATION: Lactosylated and -OH of the carboxylic acid
      terminal group is replaced with -NH2.

<400> SEQUENCE: 9

Asp Arg Val Tyr Ile His Pro Ser
1               5

<210> SEQ ID NO 10
<211> LENGTH: 7
<212> TYPE: PRT
<213> ORGANISM: Artificial Sequence
<220> FEATURE:
<223> OTHER INFORMATION: Artificial Construct
<220> FEATURE:
<221> NAME/KEY: MISC_FEATURE
<222> LOCATION: (7)..(7)
<223> OTHER INFORMATION: Glucosylated and -OH of the terminal carboxylic
      acid end is replaced with -NH2.

<400> SEQUENCE: 10

Asp Arg Val Tyr Ile His Ser
1               5

<210> SEQ ID NO 11
<211> LENGTH: 8
<212> TYPE: PRT
<213> ORGANISM: Artificial Sequence
<220> FEATURE:
<223> OTHER INFORMATION: Artificial Construct
<220> FEATURE:
<221> NAME/KEY: MISC_FEATURE
<222> LOCATION: (2)..(3)
<223> OTHER INFORMATION: Any amino acid residue
<220> FEATURE:
<221> NAME/KEY: MISC_FEATURE
<222> LOCATION: (6)..(6)
<223> OTHER INFORMATION: Any amino acid residue
<220> FEATURE:
<221> NAME/KEY: MISC_FEATURE
<222> LOCATION: (8)..(8)
<223> OTHER INFORMATION: May optionally be glucosylated or lactosylated
      and -OH of the terminal carboxylic acid end is replaced with -NH2

<400> SEQUENCE: 11

Ala Xaa Xaa Tyr Ile Xaa Pro Ser
1               5

<210> SEQ ID NO 12
<211> LENGTH: 8
<212> TYPE: PRT
<213> ORGANISM: Artificial Sequence
<220> FEATURE:
<223> OTHER INFORMATION: Artificial Construct
<220> FEATURE:
<221> NAME/KEY: MISC_FEATURE
<222> LOCATION: (3)..(3)
<223> OTHER INFORMATION: Any amino acid residue
<220> FEATURE:
<221> NAME/KEY: MISC_FEATURE
<222> LOCATION: (5)..(5)
<223> OTHER INFORMATION: Any amino acid residue
<220> FEATURE:
<221> NAME/KEY: MISC_FEATURE
<222> LOCATION: (8)..(8)
<223> OTHER INFORMATION: May optionally be glucosylated or lactosylated
      and -OH of the terminal carboxylic acid end is replaced with -NH2
```

```
<400> SEQUENCE: 12

Asp Arg Xaa Tyr Xaa His Pro Ser
1               5

<210> SEQ ID NO 13
<211> LENGTH: 8
<212> TYPE: PRT
<213> ORGANISM: Artificial Sequence
<220> FEATURE:
<223> OTHER INFORMATION: Artificial Construct
<220> FEATURE:
<221> NAME/KEY: MISC_FEATURE
<222> LOCATION: (3)..(5)
<223> OTHER INFORMATION: Any amino acid residue
<220> FEATURE:
<221> NAME/KEY: MISC_FEATURE
<222> LOCATION: (8)..(8)
<223> OTHER INFORMATION: May optionally be glucosylated or lactosylated
      and -OH of the terminal carboxylic acid end is replaced with -NH2

<400> SEQUENCE: 13

Asp Arg Xaa Xaa Xaa His Pro Ser
1               5
```

What is claimed is:

1. A heptapeptide comprising the formula: A1-A2-A3-A4-A5-A6-A7-A8 (SEQ ID NO:1) wherein
   A1 is selected from the group consisting of aspartic acid, glutamic acid, alanine, and glycosylated forms thereof;
   A2 is selected from the group consisting of arginine, histidine, lysine, and glycosylated forms thereof;
   A3 is selected from the group consisting of valine, alanine, isoleucine, leucine, and glycosylated forms thereof;
   A4 is selected from the group consisting of tyrosine, phenylalanine, tryptophan, and glycosylated forms thereof;
   A5 is selected from the group consisting of isoleucine, valine, alanine, leucine, and glycosylated forms thereof;
   A6 is selected from the group consisting of histidine, arginine, lysine, and glycosylated forms thereof;
   A7 is serine or a glycosylated form thereof; and
   A8 is absent, and wherein at least one of A1-A7 is glycosylated.

2. The heptapeptide of claim 1, wherein at least one of A1-A7 comprises a monosaccharide or disaccharide.

3. The heptapeptide of claim 2, wherein at least one of the monosaccharides or disaccharides is selected from the group consisting of glucose, galactose, xylose, fucose, rhamnose, lactose, cellobiose, and melibiose.

4. The heptapeptide of claim 1, wherein A7 is a serine that is terminated with an amino group.

5. The heptapeptide of claim 4, wherein A7 is a glycosylated serine that is terminated with an amino group.

6. The heptapeptide of claim 5, wherein the oligopeptide has the formula of SEQ ID NO: 10.

7. The heptapeptide of claim 1, wherein the oligopeptide comprises at least one D-amino acid.

8. The heptapeptide of claim 1, wherein each of A1-A7 is a D-amino acid.

9. The heptapeptide of claim 1, wherein A1 is alanine.

10. The heptapeptide of claim 9, wherein at least one of A1-A7 comprises a monosaccharide or disaccharide.

11. The heptapeptide of claim 10, wherein at least one of the monosaccharides or disaccharides is selected from the group consisting of glucose, galactose, xylose, fucose, rhamnose, lactose, cellobiose, and melibiose.

12. The heptapeptide of claim 9, wherein A7 is a glycosylated serine.

13. The heptapeptide of claim 12, wherein the A7 serine is glycosylated with glucose or lactose.

14. The heptapeptide of claim 9, wherein A7 is terminated with an amino group.

15. The heptapeptide of claim 14, wherein A7 is a glycosylated serine that is terminated with an amino group.

16. The heptapeptide of claim 9, wherein the oligopeptide comprises at least one D-amino acid.

17. The heptapeptide of claim 9, wherein each of A1-A7 is a D-amino acid.

18. A method for treating cognitive dysfunction in a subject diagnosed as having congestive heart failure, comprising administering to the patient a therapeutically effective amount of a heptapeptide having the formula: A1-A2-A3-A4-A5-A6-A7-A8 (SEQ ID NO:1) wherein
   A1 is selected from the group consisting of aspartic acid, glutamic acid, alanine, and glycosylated forms thereof;
   A2 is selected from the group consisting of arginine, histidine, lysine, and glycosylated forms thereof;
   A3 is selected from the group consisting of valine, alanine, isoleucine, leucine, and glycosylated forms thereof;
   A4 is selected from the group consisting of tyrosine, phenylalanine, tryptophan, and glycosylated forms thereof;
   A5 is selected from the group consisting of isoleucine, valine, alanine, leucine, and glvcosvlated forms thereof;
   A6 is selected from the group consisting of histidine, arginine, lysine, and glycosylated forms thereof;
   A7 is serine or a glycosylated form thereof; and
   A8 is absent.

19. The method of claim 18, wherein at least one of A1-A7 is substituted with a monosaccharide or disaccharide.

20. The method of claim 18, wherein the heptapeptide has the formula of SEQ ID NO: 10.

21. The method of claim 18, wherein the heptapeptide comprises at least one D-amino acid.

* * * * *

UNITED STATES PATENT AND TRADEMARK OFFICE
CERTIFICATE OF CORRECTION

PATENT NO. : 9,670,251 B2  
APPLICATION NO. : 15/134073  
DATED : June 6, 2017  
INVENTOR(S) : Hay et al.

Page 1 of 1

It is certified that error appears in the above-identified patent and that said Letters Patent is hereby corrected as shown below:

On the Title Page

Item (72) should read:  
Meredith Hay, Tucson, AZ (US);  
John Konhilas, Tucson, AZ (US);  
Robin L. Polt, Tucson, AZ (US);  
Evan Jones, Tucson, AZ (US);  
Lajos Szabo, Tucson, AZ (US)

Signed and Sealed this  
Twenty-second Day of October, 2019

Andrei Iancu  
*Director of the United States Patent and Trademark Office*